United States Patent [19]

Löffler

[11] Patent Number: 5,648,521
[45] Date of Patent: Jul. 15, 1997

[54] PROCESS FOR THE PREPARATION OF AMIDOPEROXYCARBOXYLIC ACIDS

[75] Inventor: Matthias Löffler, Idstein, Germany

[73] Assignee: Hoechst Aktiengesellschaft, Germany

[21] Appl. No.: 637,479

[22] Filed: Apr. 25, 1996

[30] Foreign Application Priority Data

Apr. 27, 1995 [DE] Germany ............... 195 15 443.6

[51] Int. Cl.[6] ................................. C07C 407/00
[52] U.S. Cl. ........................ 562/3; 562/2; 562/6
[58] Field of Search ........................ 562/2, 3, 6

[56] References Cited

U.S. PATENT DOCUMENTS 5,149,864  9/1992  Gethoffer et al. ............... 562/2
5,235,099  8/1993  Müller et al. ............... 562/2
5,292,451  3/1994  Gethoffer et al. ............... 252/186.42

FOREIGN PATENT DOCUMENTS 0485928  5/1992  European Pat. Off. .
0564251  10/1993  European Pat. Off. .

*Primary Examiner*—Samuel Barts
*Attorney, Agent, or Firm*—Connolly and Hutz

[57] ABSTRACT

Process for the preparation of amidoperoxycarboxylic acids, comprising the process steps: ring opening of the N-acyllactam to give the corresponding amidocarboxylic acid and, subsequently, oxidation of the resulting amidocarboxylic acid to the corresponding amidoperoxycarboxylic acid.

10 Claims, No Drawings

PROCESS FOR THE PREPARATION OF AMIDOPEROXYCARBOXYLIC ACIDS

DESCRIPTION

British Patent No. 855 735 discloses bleaches containing an inorganic peroxo salt, such as perborate, percarbonate, perhydrophosphate and persilicate, and a reactive organic acyl amide, e.g. N-acyllactam, such as N-acetylcaprolactam.

The disadvantage of these bleaches is that the necessary reactivity of the organic acyl amides to be used is dependent on certain molecular properties and thus precise predictions of the use of an acyl amide cannot be made.

This patent further relates to cleaning agents which contain an amidoperoxycarboxylic acid as bleach.

EP-A-0 564 250 relates to cleaning liquids which contain amidoperoxycarboxylic acids as bleach, amidomonoperoxycarboxylic acids and amidodiperoxycarboxylic acids being mentioned as preferred peracids. The underlying amidocarboxylic acids are prepared under the conditions of the Schotten-Baumann reaction, i.e. by reacting an amine with an acid chloride to give the corresponding carboxamide. The meaning of the term "amine" chosen in this context is broad and includes not only amines, such as piperazine and aniline, but also amino acids, such as aminobenzoic acid. By reacting these amines with the desired acid chlorides, amidomono- or amidodicarboxylic acids are obtained which are oxidized in a further reaction with a mixture of methanesulfonic acid and hydrogen peroxide to give the corresponding amidoperoxycarboxylic acids.

Disadvantages of this preparation process are the necessary use of acid chlorides, the process-related production of salt and the sometimes inadequate yield of amidoperoxycarboxylic acids.

The object of the present invention is to provide an improved process for the preparation of amidoperoxycarboxylic acids.

The present invention relates to a process for the preparation of amidoperoxycarboxylic acids, comprising the process steps:

A) ring opening of the N-acyllactam to give the corresponding amidocarboxylic acid and, subsequently, B) oxidation of the resulting amidocarboxylic acid to the corresponding amidoperoxycarboxylic acid.

The amidoperoxycarboxylic acids are preferably mono- or diamidoperoxycarboxylic acids. Monoamidoperoxycarboxylic acids preferably have the formula

in which $R^1$ is $C_1$–$C_{20}$-alkyl, $C_2$–$C_{20}$-alkenyl, $C_5$–$C_{20}$-cycloalkyl, $C_6$–$C_{18}$-aryl or $C_1$–$C_{20}$-alkyl-$C_6$–$C_{18}$-aryl and $R^2$ is $C_1$–$C_{20}$-alkylene, $C_2$–$C_{20}$-alkenylene, $C_5$–$C_{20}$-cycloalkylene, $C_6$–$C_{10}$-arylene or $C_1$–$C_{20}$-alkyl-$C_6$–$C_{18}$-arylene.

Diamidoperoxycarboxylic acids preferably have the formula

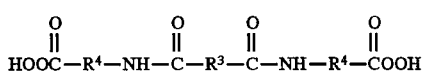

in which $R^3$ and $R^4$, independently of each other, are $C_1$–$C_{20}$-alkylene, $C_2$–$C_{20}$-alkenylene, $C_5$–$C_{20}$-cycloalkylene, $C_6$–$C_{18}$-arylene or $C_1$–$C_{20}$-alkyl-$C_6$–$C_{18}$arylene.

Particularly preferred amidoperoxycarboxylic acids are:
N,N'-di-(4-percarboxybenzoyl)-1,4-butanediamine;
N,N'-di-(4-percarhoxybenzoyl)-1,2-phenylenediamine;
N,N'-succinoyl-di-(4-percarboxy)aniline;
4-percarboxybenzoylaniline;
N,N-phthaloyl-4-aminoperbenzoic acid;
N,N'-di-(4-percarboxybenzoyl)ethylenediamine;
N,N'-di-(4-percarboxyanilino)terephthalate;
N,N,N',N'-1,2,4,5-tetracarboxybenzoyl-di-(6-aminopercarboxycaproic acid);
N,N'-di-(4-percarboxybenzoyl)piperazine;
N,N'-di-(4-percarboxybenzoyl)-1,4-diaminocyclohexane;
N,N'-di-(percarboxyadipoyl)phenylenediamine;
N,N'-di-(percarboxyadipoyl)ethylenediamine;
N,N'-terephthaloyl-di-(6-aminoperoxycaproic acid);
N,N'-terephthaloyl-di-(12-aminoperoxylauric acid) and
N,N'-oxalyl-di-(6-aminoperoxycaproic acid).

In the process of the invention, the ring opening of the N-acyllactam proceeds first to give the corresponding amidocarboxylic acid.

If the acyllactams are not available as starting materials, these may readily be prepared by reacting lactams with reactive carbonyl compounds. The syntheses described in the literature principally relate to the reaction of lactams with anhydrides (GB-A-1 102 521; U.S. Pat. No. 4,608,201) or with acid chlorides (J. Amer. Chem. Soc. 80 (1958) 6420; J. Org. Chem. 29 (1964) 2425 and Bull. Chem. Soc. Jpn. 8 (1964) 1245).

The list below gives a survey of commercial lactams and their N-acyllactams:

1. N-unsubstituted lactams
2-azetidinone
2-pyrrolidinone
    3-methyl-2-pyrrolidinone
    5-methyl-2-pyrrolidinone
2-piperidone
    6-methyl-2-piperidone
ε-caprolactam
    α-dimethylamino-ε-caprolactam
    α-amino-ε-caprolactam
    7-butyl-ε-caprolactam
    3,3-dibromo-ε-caprolactam
2-azacyclooctanone
2-azacyclononanone
2-azacyclodecanone 2. N-Acetyllactams
N-acetyl-2-azetidinone
N-acetyl-2-pyrrolidinone
N-acetyl-3-methyl-2-pyrrolidinone
N-acetyl-5-methyl-2-pyrrolidinone
N-acetyl-2-piperidone
N-acetyl-6-methyl-2-piperidone
N-acetyl-ε-caprolactam
    N-acetyl-α-dimethylamino-ε-caprolactam
    N-acetyl-ε-amino-ε-caprolactam
    N-acetyl-ε-caprolactam
    N-acetyl-3,3-dibromo-ε-caprolactam
N-acetyl-2-azacyclooctanone
N-acetyl-2-azacyclononanone
N-acetyl-2-azacyclodecanone 3. N-Benzoyllactam
N-benzoyl-2-azetidinone
N-benzoyl-2-pyrrolidinone
N-benzoyl-3-methyl-2-pyrrolidinone
    N-benzoyl-5-methyl-2-pyrrolidinone N-benzoyl-2-piperidone N-benzoyl-6-methyl-2-piperidone N-benzoyl-ε-caprolactam N-benzoyl-α-dimethylamino-ε-caprolactam N-benzoyl-α-amino-ε-caprolactam N-benzoyl-7-butyl-ε-caprolactam N-benzoyl-3,3-dibromo-ε-caprolactam N-benzoyl-2-azacyclooctanone N-benzoyl-2-azacyclononane N-benzoyl-2-azacyclodecanone 4. Other N-alkanoyllactams N-octanoyl-2-pyrrolidinone N-octanoyl-3-methyl-2-pyrrolidinone N-octanoyl-5-methyl-2-pyrrolidinone N-octanoyl-2-piperidone N-octanoyl-6-methyl-2-piperidone N-octanoyl-ε-caprolactam N-octanoyl-α-amino-ε-caprolactam N-octanoyl-3,3-dibromo-ε-caprolactam N-octanoyl-2-azacyclooctanone N-octanoyl-2-azacyclononanone N-octanoyl-2-azacyclodecanone N-decanoyl-2-pyrrolidinone N-decanoyl-3-methyl-2-pyrrolidinone N-decanoyl-5-methyl-2-pyrrolidinone N-decanoyl-2-piperidone N-decanoyl-6-methyl-2-piperidone N-decanoyl-ε-caprolactam N-decanoyl-α-amino-ε-caprolactam N-decanoyl-3,3-dibromo-4,5,6,7-tetrahydro-1H-azepin-2(3H)-one N-decanoyl-2-azacyclooctanone N-decanoyl-2-azacyclononanone N-decanoyl-2-azacyclodecanone 5. Bifunctional N-Acyllactams N,N'-terephthaloylbis-2-azetidione N,N'-terephthaloylbis-2-pyrrolidinone N,N'-terephthaloylbis-2-piperidone N,N'-terephthaloylbiscaprolactam N,N'-terephthaloylbis-2-azacyclooctanone N,N'-terephthaloylbis-2-azacyclononanone N,N'-terephthaloylbis-2-azacyclodecanone.

According to the present invention, the N-acyllactam rings are usually opened by reaction in the aqueous solution of a strong acid. Strong acids which are suitable are, preferably, sulfuric acid and methanesulfonic acid. The amount of acid is preferably one to eight times, particularly preferably three to seven times, the amount of N-acyllactam by weight. The amount of water used for ring opening is equivalent to one to ten times the molar excess, based on the carbonyl group of the N-acyllactam. The manner in which N-acyllactam, acid and water are mixed together is not critical.

If acid and water are used separately, it is advantageous to add the N-acyllactam to the acid, the N-acyllactam in many cases dissolving, and subsequently to add the water. It is likewise possible to mix N-acyllactam and water, a suspension being obtained in many cases, and subsequently to add the acid. The use of dilute acid in the amounts given above is correspondingly expedient. When sulfuric acid is used, usually, a 50 to 96% strength by weight, preferably 75 to 96% strength by weight, aqueous solution is used.

The reaction temperatures necessary for the ring opening can be selected in a broad range and are generally between 10° C. and the boiling point of the solution. Preferably, the reaction is carried out at a temperature in the range from 20° to 90° C.

The amidocarboxylic acid produced in the reaction of the N-acyllactam with acid and water is obtained in many cases in high yield. Isolation, purification or other type of workup is therefore not necessary. A great number of amidocarboxylic acids are not readily soluble in the reaction medium and can be isolated by filtration and can, if appropriate, be purified by recrystallization. Precisely because of the high yield according to the process, it is advantageous to oxidize the resulting amidocarboxylic acid to the amidoperoxycarboxylic acid directly afterwards.

The amidocarboxylic acid is oxidized with use of the conventional oxidizing agent, preferably hydrogen peroxide. The oxidation preferably proceeds at mild temperatures, preferably between −5° and 40° C., particularly preferably between 20° and 35° C. The hydrogen peroxide solution used has a commercially conventional concentration, preferably 25 to 85% strength by weight solution.

The oxidizing agent is used in a one- to ten-fold, preferably two- to four-fold, molar excess, based on the carboxyl groups of the amidocarboxylic acid.

The amidoperoxycarboxylic acids obtained in this manner are produced in high yields and may be precipitated out by addition of water. By adding aqueous basic salts, the corresponding salts may be obtained. Purification is possible by recrystallization.

The advantages of the process of the invention are, inter alia, the avoidance of the use of acid chloride, the reduction of the salt production previously entailed and the preparation of the amidoperoxycarboxylic acid without isolation of the intermediates from process step (A).

Preparation examples:

Example 1

N,N'-Terephthaloylbiscaprolactam

Terephthaloyl chloride (51 g, 0.25 mol) is added in the course of 30 minutes to a solution of ε-caprolactam (56.6 g, 0.5 mol) in 400 ml of cyclohexane and 117 ml of pyridine at room temperature. The mixture is then refluxed for 4 h. After cooling, the resulting light yellow precipitate is filtered off by suction, washed with water and dried. Yield 81 g (91%).

N,N'-Terephthaloyl-di-(6-aminoperoxycaproic acid)

70 g of concentrated sulfuric acid are added dropwise in the course of one hour to a liquid mixture of N,N'-terephthaloylbiscaprolactam (17.9 g, 50 mmol) and water (4.0 g, 220 mmol) at 80° C. After the reaction solution is cooled to 20° C, 25 ml of 70% strength aqueous hydrogen peroxide solution are added dropwise. The internal temperature is kept between 30° and 35° C. during this by ice cooling. After one hour, a further 5 ml of 70% strength hydrogen peroxide solution are added dropwise and the mixture is further stirred for one hour at 30° to 35° C. 500 ml of ice water are then added to the reaction batch, the resulting colorless precipitate is filtered off by suction and washed to neutrality with water. Yield 21.0 g (99 %), active oxygen content 6.7 % (89.3 %).

Example 2

N,N'-Terephthaloylbislaurolactam

Terephthaloyl chloride (203 g, 1 mol) is added in the course of 30 minutes to a solution of ω-laurolactam (403 g, 2 mol) in 1600 ml of cyclohexane and 475 ml of pyridine at room temperature. The mixture is then refluxed for 3 h. After cooling, the flask contents are poured into 3 l of ice water and the resulting light yellow precipitate is filtered off by suction and dried. Yield 498 g (95%).

N,N'-Terephthaloyl-di-(12-aminoperoxylauric acid)

A suspension of N,N'-terephthaloylbislaurolactam (26.2 g, 50 mmol) in water (4.0 g, 220 mmol) and concentrated sulfuric acid (100 g) is stirred for 4 h at 25° C. 30 ml of 70% strength aqueous hydrogen peroxide solution are then added dropwise in the course of one hour, and the internal temperature is kept between 30° and 35° C. during this by ice cooling. After further stirring for one hour, the reaction batch is admixed with 500 ml of ice water, the resulting colorless precipitate is filtered off by suction and washed to neutrality with water. Yield 27.3 g (98%), active oxygen content 5.0% (86.5%).

Example 3

N-Benzoyl-6-aminoperoxycaproic acid 140 g of sulfuric acid are added dropwise in the course of half an hour to a liquid mixture of N-benzoyl-caprolactam (21.7 g, 100 mmol) and water (8.0 g, 440 mmol) at 68° C. The internal temperature increases in the course of this to 80° C., and the mixture is further stirred for 1 hour at this temperature. After the reaction solution is cooled to 20° C., 42 ml of 50% strength aqueous hydrogen peroxide solution are added dropwise. The internal temperature is kept between 25° and 30° C. during this by ice cooling. After one hour, the reaction batch is admixed with 500 ml of ice water, and the resulting colorless precipitate is filtered off by suction and washed to neutrality with water. Yield 22.2 g (88%), active oxygen content 6.2 % (98%).

Example 4

N,N'-Oxalylbiscaprolactam

Oxalyl dichloride (63.4 g, 0.5 mol) is added dropwise in the course of 30 minutes to a solution of ε-caprolactam (107.6 g, 0.95 mol) in toluene (300 ml). The internal temperature increases in the course of this from 20 to 60° C. The mixture is then refluxed for 2 hours. After removal of the solvent in vacuo, the resulting oil is taken up in methanol, the colorless precipitate precipitating out in the cold is isolated and dried. Yield 113.8 g (86%).

N,N'-Oxalyl-di-(6-aminoperoxycaproic acid)

A suspension of N,N'-oxalylbiscaprolactam (14.17 g, 50 mmol) in water (1.8 g, 100 mmol) and concentrated sulfuric acid (50 g) is stirred at room temperature for four hours. 50% strength by weight hydrogen peroxide solution (40.8 g) is then added dropwise with ice cooling in such a manner that the internal temperature does not exceed 25° C. After stirring for one hour at 30° C., water (250 ml) is added, and the resulting colorless precipitate is filtered off by suction, washed to neutrality with water and dried. Yield 15.5 g, (89%), active oxygen 8.8% (96%).

I claim:

1. A process for the preparation of amidoperoxycarboxylic acids, comprising the process steps:
   A) ring opening of the N-acyllactam to give the corresponding amidocarboxylic acid and, subsequently,
   B) oxidation of the resulting amidocarboxylic acid to the corresponding amidoperoxycarboxylic acid.

2. The process as claimed in claim 1, wherein, in process step (A), the N-acyllactam ring is opened in the aqueous solution of a strong acid.

3. Process as claimed in claim 1, wherein in step (A), the N-acyllactam ring is opened in the aqueous solution of a strong acid wherein the amount of the strong acid is one to eight times the amount by weight of the N-acyllactam.

4. The process as claimed in claim 1, wherein the amount of water used in process step (A) corresponds to one to ten times the molar excess, based on the carbonyl group of the N-acyllactam.

5. The process as claimed in claim 1, wherein, in process step (A), methanesulfonic acid or sulfuric acid is used.

6. The process as claimed in claim 1, wherein, in process step (A), 50 to 96% strength by weight aqueous sulfuric acid is used.

7. The process as claimed in claim 1, wherein, in process step (A), the ring is opened at a reaction temperature between 10° C. and the boiling point of the solution.

8. The process as claimed in claim 1, wherein, in process step (B), the amidocarboxylic acid is oxidized by hydrogen peroxide.

9. The process as claimed in claim 1, wherein the oxidation is carried out at a temperature between −5° and 40° C.

10. The process as claimed in claim 1, wherein process step (B) is carried out subsequently to process step (A) without isolation of the amidocarboxylic acid.

* * * * *